(12) United States Patent
Frushour

(10) Patent No.: US 10,675,100 B2
(45) Date of Patent: Jun. 9, 2020

(54) SYSTEMS AND METHODS FOR IMPROVING MEDICAL INSTRUMENTS AND DEVICES

(71) Applicant: COVIDIEN LP, Mansfield, MA (US)

(72) Inventor: Scott E.M. Frushour, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 426 days.

(21) Appl. No.: 15/450,761

(22) Filed: Mar. 6, 2017

(65) Prior Publication Data
US 2018/0250093 A1    Sep. 6, 2018

(51) Int. Cl.
| | | |
|---|---|---|
| A61B 18/12 | (2006.01) |
| A61B 34/00 | (2016.01) |
| A61B 90/98 | (2016.01) |
| A61B 90/94 | (2016.01) |
| A61B 90/96 | (2016.01) |
| A61B 90/00 | (2016.01) |

(52) U.S. Cl.
CPC .......... *A61B 34/25* (2016.02); *A61B 18/1206* (2013.01); *A61B 90/94* (2016.02); *A61B 90/96* (2016.02); *A61B 90/98* (2016.02); *A61B 2034/256* (2016.02); *A61B 2090/0803* (2016.02); *A61B 2090/0804* (2016.02)

(58) Field of Classification Search
CPC ......... A61B 90/90; A61B 90/94; A61B 90/98; A61B 18/1206; A61B 34/25; A61B 2034/256; G06F 19/30; G06F 19/32; G06F 19/36
See application file for complete search history.

(56) References Cited

U.S. PATENT DOCUMENTS

| | | | |
|---|---|---|---|
| 6,733,495 B1 * | 5/2004 | Bek | A61B 18/00 606/34 |
| 7,118,029 B2 | 10/2006 | Nycz et al. | |
| 7,268,684 B2 | 9/2007 | Tethrake et al. | |
| 7,577,573 B2 | 8/2009 | Janas, III et al. | |
| 8,126,729 B2 | 2/2012 | Dicks et al. | |
| 8,310,336 B2 | 11/2012 | Muhsin et al. | |
| 8,454,613 B2 | 6/2013 | Tethrake et al. | |
| 8,521,716 B2 | 8/2013 | Uber, III et al. | |
| 9,204,920 B2 * | 12/2015 | McPherson | A61B 18/1206 |

(Continued)

FOREIGN PATENT DOCUMENTS

| | | |
|---|---|---|
| WO | 2016044920 A1 | 3/2016 |
| WO | 2016059382 A1 | 4/2016 |

*Primary Examiner* — Michael F Peffley

(57) ABSTRACT

Systems and methods are provided for improving medical instruments and devices. One system includes a surgical instrument associated with an instrument identifier, and an electrosurgical generator operably coupled to the surgical instrument. The electrosurgical generator is associated with a generator identifier and is configured to receive and store data associated with an operating mode of the surgical instrument, receive data associated with the instrument identifier from the surgical instrument, generate a unique identifier based on a time and date at which the surgical instrument is operably coupled with the electrosurgical generator for the first time, the generator identifier of the electrosurgical generator, and the instrument identifier, and associate the unique identifier with the stored data associated with the operating mode of the surgical instrument.

22 Claims, 8 Drawing Sheets

(56) References Cited

U.S. PATENT DOCUMENTS

| | | | |
|---|---|---|---|
| 2006/0136167 A1* | 6/2006 | Nye | A61B 5/02055 |
| | | | 702/127 |
| 2008/0262654 A1* | 10/2008 | Omori | A61B 90/96 |
| | | | 700/245 |
| 2009/0099876 A1 | 4/2009 | Whitman | |
| 2009/0106692 A1 | 4/2009 | Bhavani | |
| 2010/0262139 A1* | 10/2010 | Beller | A61B 18/1206 |
| | | | 606/41 |
| 2011/0022411 A1 | 1/2011 | Hjelm et al. | |
| 2011/0161098 A1 | 6/2011 | Haider et al. | |
| 2011/0167373 A1* | 7/2011 | Van Vlimmeren | G06F 19/36 |
| | | | 715/772 |
| 2013/0190674 A1 | 7/2013 | Case et al. | |
| 2015/0213223 A1 | 7/2015 | Amarasingham et al. | |
| 2015/0317899 A1* | 11/2015 | Dumbauld | G08B 21/245 |
| | | | 340/540 |
| 2016/0055359 A1* | 2/2016 | Jensen | G06K 7/10366 |
| | | | 340/10.5 |
| 2017/0024522 A1* | 1/2017 | Warner | G16H 10/65 |

\* cited by examiner

SYSTEMS AND METHODS FOR IMPROVING MEDICAL INSTRUMENTS AND DEVICES

TECHNICAL FIELD

The present disclosure generally relates to methods and systems for improving medical instruments and devices. More particularly, the present disclosure relates to systems and methods for improving medical instruments and devices based on outcomes of medical procedures performed on patients and how instruments were used during the medical procedures.

BACKGROUND

Current medical procedures, typically, require use of multiple complex medical instruments and devices. However, identifying areas of improvements in these complex medical instruments and devices is inefficient and ineffective because sufficient real-world empirical data to precisely identify an area of improvement that will improve the likelihood of successful outcomes of the medical procedure is unavailable.

For example, in electrosurgery, surgical instruments configured to perform electrosurgery are plugged into and supplied energy by an electrosurgical generator. The electrosurgical generators and instruments provide a plurality of operating modes, which allow precise control over the supply of current to surgical instruments when utilized by a clinician. Inputs to electrosurgical generators or surgical instruments connected to the electrosurgical generators typically cause them to operate in one of the operating modes over another. The electrosurgical generators capture information about the different inputs. The information about the different inputs may be made available to a medical device manufacturer. However, such information alone is insufficient for the medical device manufacturer to effectively and efficiently identify instruments or devices that need to be improved or even identify areas of improvement within a particular instrument or device because such information does not indicate whether the medical procedure performed using these different inputs to the electrosurgical generator or surgical instruments was successful.

SUMMARY

According to an aspect of the present disclosure, systems and methods are provided that address the above mentioned needs. In an aspect of the present disclosure, a system is provided that includes a surgical instrument associated with an instrument identifier and an electrosurgical generator operably coupled to the surgical instrument. The electrosurgical generator is associated with a generator identifier and is configured to receive and store data associated with an operating mode of the surgical instrument, receive data associated with the instrument identifier from the surgical instrument, generate a unique identifier based on a time and date at which the surgical instrument is operably coupled with the electrosurgical generator for the first time, the generator identifier of the electrosurgical generator, and the instrument identifier, and associate the unique identifier with the stored data associated with the operating mode of the surgical instrument.

In another aspect of the present disclosure, the electrosurgical generator is further configured to store the unique identifier in a storage device operably coupled to a wireless communication device of the electrosurgical generator.

In another aspect of the present disclosure, the wireless communication device is a radio frequency identification tag.

In still another aspect of the present disclosure, the wireless communication device a near field communication tag.

In still another aspect of the present disclosure, the generator identifier includes a serial number of the electrosurgical generator.

In still another aspect of the present disclosure, the instrument identifier includes a serial number of the surgical instrument.

In yet another aspect of the present disclosure, the electrosurgical generator is further configured to record the time and date at which the surgical instrument is operably coupled with the electrosurgical generator for the first time.

In yet another aspect of the present disclosure, the electrosurgical generator is further configured to store real-time data related to the surgical instrument during the medical procedure, and associate the unique identifier with the stored real-time data related to the surgical instrument.

In yet another aspect of the present disclosure, the electrosurgical generator further includes a display, and is further configured to display the unique identifier on the display.

In yet another aspect of the present disclosure, the system further comprises a handheld computing device including an image capture device, a processor, and a memory, the memory having instructions stored thereon which, when executed, cause the handheld computing device to: capture an image of the unique identifier displayed on the display of the electrosurgical generator, and associate the captured image of the unique identifier to outcome data of the medical procedure.

In still another aspect of the present disclosure, the instructions stored on the memory of the handheld computing device further cause the handheld computing device to display a graphical user interface including input buttons for inputting the outcome data of the medical procedure.

According to another aspect of the present disclosure, a method is provided and the method includes, receiving data associated with an operating mode of a surgical instrument, storing the data associated with the operating mode of the surgical instrument, receiving data associated with an instrument identifier from the surgical instrument, generating a unique identifier based on a time and date at which the surgical instrument is operably coupled with an electrosurgical generator for the first time, the data associated with a generator identifier of the electrosurgical generator, and the data associated with the instrument identifier, and associating the unique identifier with the stored data associated with the operating mode of the surgical instrument.

In yet another aspect of the present disclosure, the method further includes storing the unique identifier in a storage device operably coupled to a wireless communication device.

In yet another aspect of the present disclosure, the wireless communication device is a radio frequency identification tag.

In still another aspect of the present disclosure, the wireless communication device is a near field communication tag.

In still another aspect of the present disclosure, the generator identifier includes a serial number of the electrosurgical generator.

In still another aspect of the present disclosure, the instrument identifier includes a serial number of the surgical instrument.

In yet another aspect of the present disclosure, the method further includes recording the time and date at which the surgical instrument is operably coupled with the electrosurgical generator for the first time.

In yet another aspect of the present disclosure, the method further includes storing real-time data related to the surgical instrument during the medical procedure, and associating the unique identifier with the stored real-time data related to the surgical instrument.

In yet another aspect of the present disclosure, the method further includes displaying the unique identifier on a display of the electrosurgical generator.

In yet another aspect of the present disclosure, the method further includes capturing, using an image capturing apparatus of a handheld computing device, an image of the unique identifier displayed on the display of the electrosurgical generator, and associating the captured image of the unique identifier to outcome data of the medical procedure.

In still another aspect of the present disclosure, the method further includes, on the handheld computing device, displaying a graphical user interface including input buttons for inputting outcome data of the medical procedure.

BRIEF DESCRIPTION OF THE DRAWINGS

The above and other aspects, features, and advantages of the present disclosure will become more apparent in light of the following detailed description when taken in conjunction with the accompanying drawings, in which.

DETAILED DESCRIPTION

The present disclosure is directed to systems and methods that improve the usability of data collected by surgical instruments and/or electrosurgical generators during a medical procedure. In particular, the systems and methods receive and store instrument usage data during a medical procedure performed on a patient, generate a unique identifier and associate the instrument usage data with the unique identifier, receive and store outcome data of the medical procedure, and associate the generated unique identifier with the outcome data of the medical procedure.

The stored instrument usage data includes: the surgical instruments that were used; the various operating modes in which the surgical instruments operated in during the medical procedure; the various inputs to the surgical instruments; the various operating modes in which the electrosurgical generator operated in during the medical procedure; the various settings of the electrosurgical generator during the medical procedure; and the like. The outcome data of the medical procedure is received and stored on a handheld computing device. The handheld computing device also receives the unique identifier and associates the unique identifier with the outcome data of the medical procedure.

By utilizing these data, the usage data of the electrosurgical generator and associated instruments may be associated to a particular medical procedure during which a specific and unique outcome for the patient was delivered. In this way, medical device manufacturers may gather and analyze the data and identify correlations between the specific and unique outcome of the medical procedure and usage patterns of instruments used during the medical procedure in order to identify areas of improvements in the instruments and devices used during the medical procedure to deliver improved outcomes to the patient's health. Additionally, such data may be provided to medical facilities and/or clinicians to provide quantifiable measurements of a clinician's process to improve the clinician's skills.

As used herein, the term "clinician" refers to a doctor, a nurse, or any other care provider and may include support personnel. Throughout this description, the term "proximal" refers to the portion of the device or component thereof that is farthest from the patient and the term "distal" refers to the portion of the device or component thereof that is closest to the patient. Throughout this description, the term "publish" refers to making data available for consumption or retrieval by other computing devices. Throughout the description, the term "outcome data" refers to data that describes the observations and effects of a medical procedure.

Figure 1:
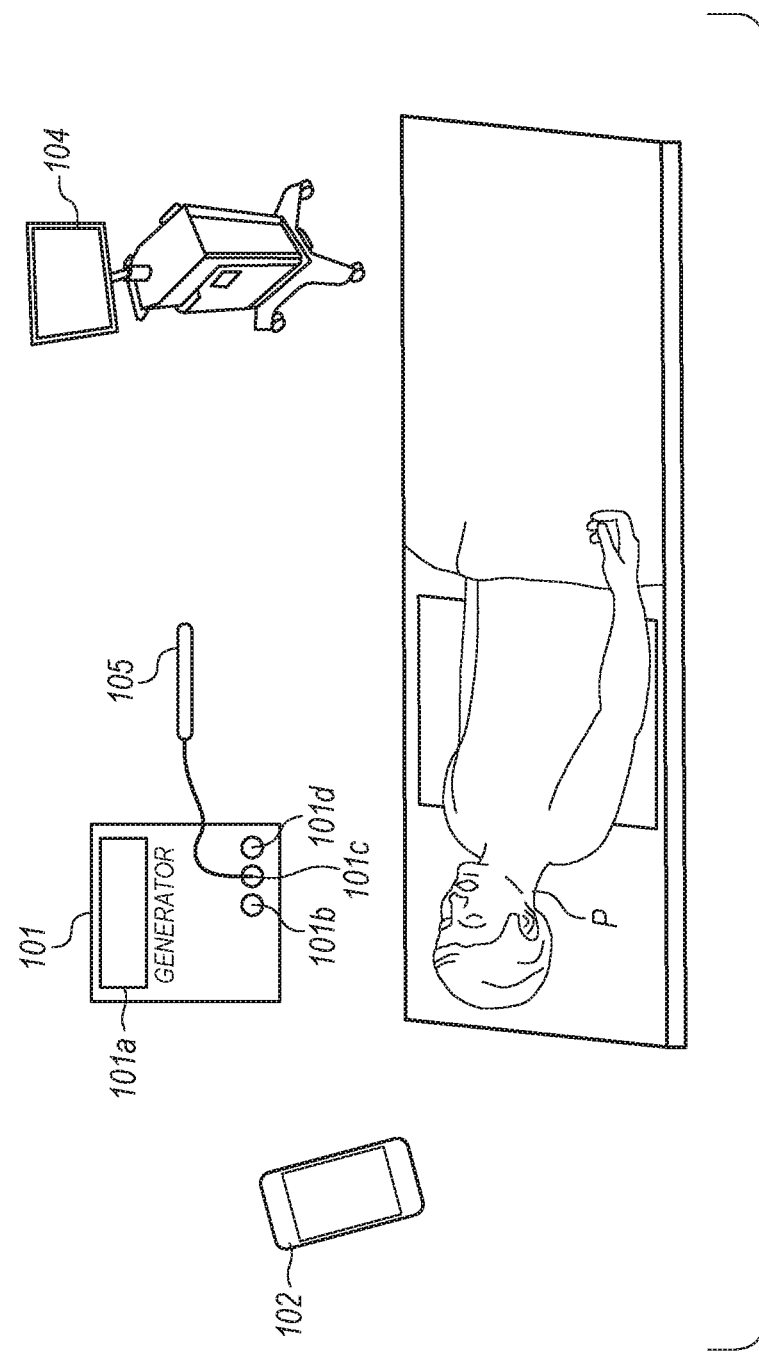
FIG. 1 is a schematic of an integrated surgical system, in accordance with an embodiment of the present disclosure, for use with a handheld computing device.

With reference to FIG. 1, a surgical system (referred to herein as "system") 100 is provided for associating instrument usage data during a medical procedure with outcome data of the medical procedure. The system 100 may be used with a mobile computing device, such as handheld computing device 102, which can be used to further associate the outcome data with patient data. The handheld computing device 102 may be any type of mobile computing device, including, but not limited to, a smartphone, a tablet computer, etc. The specific number of components of the system 100 depicted in FIG. 1 and the arrangement and configuration thereof are provided for illustrative purposes only and should not be construed as limiting. For instance, various embodiments herein employ fewer or greater than all of the components shown in FIG. 1. Additionally, the system 100 depicted in FIG. 1 is provided as an example context in which various example embodiments herein are applicable. However, the various example embodiments herein are also applicable in contexts other than integrated surgical systems, for example, in reviewing the manner in which a surgical procedure was performed for instructional purposes.

The system 100 is configured to perform various electrosurgical procedures on patients, such as patient "P". In this regard, the system 100 includes an electrosurgical generator 101, a workstation 104, and a surgical instrument 105. The electrosurgical generator 101 includes electronic circuitry (not shown) configured to generate and supply radio frequency (RF) energy to the surgical instrument 105 operably connected to the electrosurgical generator 101. The electrosurgical generator 101 is further configured to receive inputs from devices, users or both, and to output RF waveforms based on the received inputs. For example, the electrosurgical generator 101 receives an input indicating a selection of an operating mode of the electrosurgical instrument 105, and in response to the received input, outputs a RF waveform that corresponds to the selected operating mode. In another embodiment, the electrosurgical generator 101 has a user interface at which the user may provide an input to select or adjust the RF waveform.

The user interface of the electrosurgical generator 101 includes a plurality of input controls (not shown). As described herein, the term "input control" refers to a mechanism or method that transmits an input signal or message to the electrosurgical generator 101 and that controls the electrosurgical generator 101 or affects the output of the electrosurgical generator 101 or both. Examples of input controls include, but are not limited to, switches, knobs, activators, buttons, touch screens, etc. The user interface of the electrosurgical generator 101 may further include graphical user interfaces (not shown) that present a plurality of input control options to a clinician. For example, using a touch screen displaying a graphical user interface, electrosurgical generator 101 may present a plurality of graphical items to a clinician, where selection of some of the graphical items transmit input messages to the electrosurgical generator 101 that control and affect the outcome of the electrosurgical generator 101, while selection of the other graphical items present additional graphical items and selection of some of the additional graphical items transmit input messages to the electrosurgical generator 101 that control and affect the output of the electrosurgical generator 101. The term "graphical items" as used herein includes, but is not limited to, images, graphical labels, data entry mechanisms, such as text boxes, radio buttons, drop down lists, drop down menus, etc., or combinations thereof.

The electrosurgical generator 101 is configured to operate in a plurality of operating modes including, but not limited to, a low cutting mode for cutting delicate tissue, a pure cutting mode for cutting tissue cleanly and precisely, a blend cutting mode for cutting tissue with hemostasis, a desiccate coagulation mode for delicate tissue, a fulgurate coagulation mode, a spray coagulation mode for coagulation large areas of tissue, a plurality of bipolar modes that utilize different levels of voltage, a plurality of monopolar modes, etc. In an embodiment, the operating modes of the electrosurgical generator 101 may be selected using the user interface of the electrosurgical generator 101. In another embodiment, the electrosurgical generator 101 may be configured to change its operating modes based on a signal received from an external device, such as an electrosurgical instrument. For example, a clinician may make a selection of an operation to be performed on an electrosurgical instrument, which transmits the selection to the electrosurgical generator 101, and, in response, the electrosurgical generator 101 changes to an operating mode that corresponds with the selection on the electrosurgical instrument.

The electrosurgical generator 101 further includes a display 101a used to display various information. In some embodiments, the electrosurgical generator 101 may be further configured to store certain information in one or more wireless communication devices including, but not limited to, radio frequency identification (RFID) tags, near-field communication (NFC) tags, etc.

The electrosurgical generator 101 further includes one or more ports, such as ports 101b, 101c, 101d, that are configured to receive various types of electrosurgical instruments, such as the electrosurgical instrument 105. In FIG. 1, the electrosurgical instrument 105 is operably coupled to the electrosurgical generator 101 via its connection to port 101b. The electrosurgical instrument 105 may be any type of electrosurgical instrument, such as a monopolar electrosurgical instrument, a bipolar electrosurgical forceps, etc. The electrosurgical instrument may be operably coupled to the workstation 104. The workstation 104 is configured to allow a clinician to plan the navigation of the electrosurgical instrument 105 to a surgical site within the patient P. The workstation 104 may be configured to allow a clinician to monitor the position of the electrosurgical instrument 105 within the patient P. While a single electrosurgical instrument is depicted in FIG. 1, those skilled in the art will appreciate that a plurality of electrosurgical instruments may be utilized within system 100 during a surgical procedure performed on patient P using system 100.

Each electrosurgical instrument used in system 100, including the electrosurgical instrument 105, may operate in a plurality of operating modes including, but not limited to, cutting mode, coagulation mode, vessel sealing mode, etc. The electrosurgical instruments used in system 100 may provide finer control of each operating mode. For example, the electrosurgical instruments may allow a clinician to select a low cutting mode for cutting delicate tissue, a pure cutting mode for cutting tissue cleanly and precisely, a blend cutting mode for cutting tissue with hemostasis, desiccate coagulation mode for delicate tissue, fulgurate coagulation mode, spray coagulation mode for coagulation large areas of tissue. The electrosurgical instruments used in system 100 may be configured to transmit the selected operating mode to the electrosurgical generator 101. As described above, the electrosurgical generator 101 may switch its operating mode to that which corresponds with the selected operating mode.

Each electrosurgical instrument used in system 100, including the electrosurgical instrument 105, is associated with an instrument identifier, such as a unique serial number. When the electrosurgical instrument 105 is operably coupled to the electrosurgical generator 101, the electrosurgical generator 101 identifies the instrument identifiers of the electrosurgical instruments. The electrosurgical generator 101 is configured to use at least one of the instrument identifiers to generate a unique identifier for the procedure being performed on patient P. Additional details of the generation of the unique identifier are described below with reference to FIGS. 2, 3, and 5.

Figure 2:
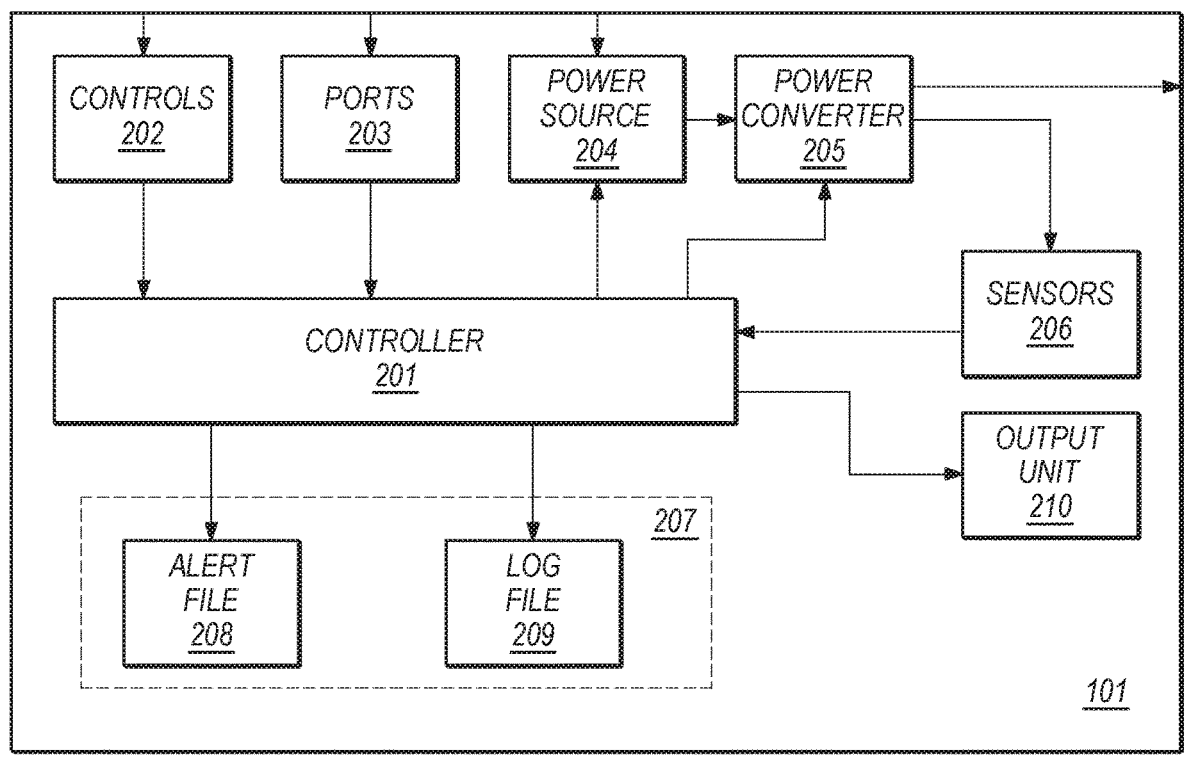
FIG. 2 is a block diagram of an electrosurgical generator, in accordance with an embodiment of the present disclosure.

Turning now to FIG. 2, there is shown a block diagram of the electrosurgical generator 101. The electrosurgical generator 101 includes a controller 201, a controls unit 202, a ports unit 203, a power source 204, a power converter 205, sensors 206, a storage device 207, an alert file 208, a log file 209, and an output unit 210. The controls unit 202 is configured to capture and identify the inputs received by the electrosurgical generator 101 from the input controls of the electrosurgical generator 101 and transmit the inputs or the information associated with the inputs to the controller 201 or both. The ports unit 203 is configured to identify the ports in which the electrosurgical instruments are plugged into, identify certain information about the electrosurgical instruments, such as the instrument identifiers (for example, unique serial numbers) of the electrosurgical instruments, etc., and transmit that information to the controller 201. The ports unit 203 is also configured to transmit input signals received from the electrosurgical instruments that are operably coupled to or plugged into the ports of the electrosurgical generator 201 to the controller 201. While the controls unit 202 and the ports unit 203 are depicted in blocks outside of the controller 201, one skilled in the art will appreciate that the necessary circuitry and logic of the controls unit 202 and the ports unit 203 may be included within the controller 201. In other words, the controller 201 may include the controls unit 202 and the ports unit 203.

The power source 204 may be connected to an alternating current (AC) source and configured to supply a high voltage direct current (DC) power to the power converter 205. The power converter 205 converts the high voltage DC power into radio frequency (RF) energy and delivers the RF energy to an active terminal (not shown) of the electrosurgical instrument operably coupled to the electrosurgical generator 101. The power converter 205 is operably coupled to the active and return terminals of the electrosurgical instrument. In embodiments where the electrosurgical instrument is a monopolar electrosurgical instrument, the power converter 205 is operably coupled to the active electrode of the monopolar electrosurgical instrument and to the return electrode pad. In embodiments where the electrosurgical instrument is a bipolar electrosurgical instrument, the power converter 205 is operably coupled to the active electrode and to the return electrode of the bipolar electrosurgical instrument.

The power converter 205 is configured to operate in a plurality of operating modes, and is configured to output electrical waveforms based on a selected operating mode. The operating modes may correspond to operations that a clinician desires the system 100 to perform. For example, different operating modes of the power converter 205 may correspond to sealing of vessels, cutting delicate tissue, cutting tissue cleanly and precisely, cutting with hemostasis, desiccation of tissue, fulguration of tissue, fulguration of tissue without contact, coagulation of tissue, coagulation of large areas of tissue, etc. The electrical waveforms may differ from each other and each waveform may correspond to a certain operating mode. For example, the power converter 205 may change the output electrical waveform with a particular duty cycle to a different electrical waveform with a different duty cycle based on the operating mode of the power converter 205. In some embodiments, the power converter 205 may be configured to be a resonant RF amplifier. The transition from one operating mode of the power converter 205 to another operating mode of the power converter 205 may be controlled or determined by the controller 201.

The sensors 206 are operably coupled to the power converter 205 and are configured to measure a plurality of electrical properties output by the power converter 205 including, but not limited to, current, voltage, RF energy, etc. In some embodiments, one or more additional sensors may be operably coupled to the power source 204 and transmit to the controller 201, the measurements of the power being supplied to the power converter 205 from the power source 205. The sensors 206 may be further configured to transmit the measurements of the electrical properties output by the power converter 205 to the controller 201.

The controller 201 includes one or more processors (not shown) that are operably connected to one or more of a memory (not shown). The memory may be any type of hardware device used to store data. The memory may be volatile memory, such as random access memory (RAM) (e.g., dynamic random access memory (DRAM), static random access memory (SRAM), etc.). The memory may be non-volatile memory, such as read-only memory (ROM) (e.g., programmable read-only memory (EPROM), electrically erasable programmable read-only memory (EEPROM), non-volatile RAM (NVRAM), etc.). The memory may also be magnetic, optical, or electrical media. The memory may store instructions to be executed by the one or more processors, and the techniques described herein are performed by the electrosurgical generator 101 in response to the one or more processors executing one or more sequences of the one or more instructions stored in the memory.

The one or more processors may be any type of suitable processor that is adapted to perform or execute the techniques or operations or instructions described herein. For instance, the processors may be hardware processors programmed to perform the techniques described herein pursuant to the instructions in firmware, memory, or other storage, or a combination thereof. Similarly, the processors may also be one or more application specific integrated circuits (ASICs), field programmable gate arrays (FPGAs) that are persistently programmed to perform the techniques or operations described herein. The processors may also be a central processing unit (CPU), a digital signal processor (DSP), a microprocessor, or any other device that incorporates hard wired logic or program logic or both to perform the operations or techniques described herein.

The controller 201 is operably coupled to the power source 204 and the power converter 205. The controller 201 is further configured to control the output of the electrosurgical generator 101 by controlling the power source 204 and the power converter 205. For instance, the controller 201 may control the output of the electrosurgical generator 101 by adjusting the power supplied to the power converter 205 or the output from the power converter 205 or both, based on the inputs from the sensors 206. Similarly, the controller 201 may adjust the power supplied to the power converter 205 or the output from the power converter 205 or both, based on the inputs from the controls unit 202 or the ports unit 203 or both. For example, the ports unit 203 transmits to the controller 201 a signal or data that indicates that the clinician, on the electrosurgical instrument that is operably coupled to the electrosurgical generator 101, selected an operation mode configured for coagulation. Then, based on the input from the ports unit 203, the controller 201 adjusts the amount of power supplied to the power converter 205 or the amount of power delivered from the power converter 205 to generate a RF waveform, with the desired shape, duty cycle, energy intensity, or a combination thereof, suitable for coagulating tissue.

The controller 201 is further configured to perform various mathematical computations to control the power source 204 or power converter 205 in generating the desired RF waveforms. For example, the controller 201 may calculate the power level or intensity of the output of the electrosurgical generator and adjust the power source 204 or power converter 205, based on the calculated power level or intensity. Other examples of the mathematical computations include, but are not limited to, calculating amount of energy being delivered, load impedance, various other types of power levels (e.g., instantaneous power levels, root mean square (RMS) power levels, etc.).

The controller 201 is operably coupled to a storage device 207. The storage device 207 may be any type of hardware device used to store information including, but not limited to, volatile memory, non-volatile memory, magnetic storage media, optical storage media, electrical storage media, etc. The storage device 207 includes the alert file 208 and the log file 209. In some embodiments, the alert file 208 and the log file 209 may be text files. The contents of the alert file 208 and the log file 209 are described below. The controller 201 is configured to write data to or store data in the storage device 207. In particular, the controller 201 is configured to store in the storage device 207 data corresponding to instrument usage during a medical procedure. The term "instrument usage" refers to how the various electrosurgical instruments, such as electrosurgical instrument 105, and electrosurgical generators, such as electrosurgical generator 101, were used during a medical procedure. Examples of data corresponding to instrument usage during a medical procedure includes data corresponding to the various operation modes of the electrosurgical instruments, data corresponding to the inputs to the electrosurgical instruments during the medical procedure, data corresponding to the inputs to the electrosurgical generator 101 during the medical procedure, the outputs of the electrosurgical generator 101 during the medical procedure, alerts or warnings received by or generated by the electrosurgical generator 101 during the medical procedure, inputs to the controller 201, such as the electrical properties measured by the sensors 206, outputs of the controller 201, such as outputs from the controller 201 and inputs to the power source 204, the power converter 205, output unit 210, or computations performed by the controller 201, etc.

The controller 201 may be further configured to write or store the instrument usage data in the log file 209 and also store all the alerts or warnings received or generated by the electrosurgical generator 101 or the controller 201 in the alert file 209. The controller 201 may also store or write a timestamp in the alert file 208 and/or the log file 209 along with data entries made to the alert file 208 and the log file 209. The timestamps entered into the alert file 208 or log file 209 may represent the date and time at which the event that is being described in the data entry occurred. For example, the controller 201, when storing data corresponding to an input to the electrosurgical generator 101, may store a time stamp that represents the date and time at which the input was received by the electrosurgical generator 101.

The timestamps may also represent the date and time at which data entries are made to the alert file 208 or the log file 208 by the controller 201. In some embodiments, the controller 201 may store the date and time at which the event that is being described in the data entry occurred and the date and time at which the data entry is made in the log file 208 or the alert file 209. For example, the controller 201 may begin an entry in the log file 208 with a first time stamp that represents the date and time at which the controller 201 is storing data in or writing to the log file 208 and may also include a second timestamp that represents the date and time at which input was received by the electrosurgical generator 101. In some embodiments, the controller 201 may create and store a new alert file and a new log file in the storage device for each electrosurgical instrument that is operably coupled to the electrosurgical generator 101, and store data associated with a particular electrosurgical instrument only in the alert file and the log file associated with the particular electrosurgical instrument. For example, if N number of electrosurgical instruments are operably coupled to the electrosurgical generator 101, then the controller 201 creates N number of log files and N number of alert files in the storage device and each of the N log files and alert files will only be associated with one electrosurgical instrument, and the controller 201 stores data of that electrosurgical instrument in the alert file and the log file associated with that electrosurgical instrument.

While the storage device 207 is, in FIG. 2, depicted in the block outside of controller 201, one skilled in the art will appreciate that the storage device 207 may be included within controller 201 and that the controller 201 may be configured with the necessary circuitry and logic to read data from or access data from and write data to or store data in the storage device 207, including the alert file 208 and the log file 209.

The controller 201 is further configured to generate a unique identifier, which is used to associate outcome data of a medical procedure with data corresponding to the instrument usage during the medical procedure. As described above, the term "outcome data" as used herein refers to data that include the quantitative and qualitative observations made during a medical procedure and post medical procedure. Examples of outcome data are the patient's length of stay, the amount of blood lost during the procedure, the time at which the procedure was performed, the type of the medical procedure that was performed, effects of a medical procedure on the health of the patient, etc. Outcome data is typically captured and recorded by a clinician after the medical procedure is performed.

The controller 201 generates the unique identifier based on one or more unique identifying codes. Examples of unique identifying codes include, but are not limited to, instrument identifiers, such as serial numbers of products such as electrosurgical instruments and/or electrosurgical generators, a time at which the process of generating the unique identifier begins, etc. The controller 201 may generate the unique identifier for the medical procedure based on a combination of the serial number of the first electrosurgical instrument that is plugged into or operably coupled to the electrosurgical generator 101, the serial number of the electrosurgical generator 101, and the date and time at which the first electrosurgical instrument is plugged into or operably coupled to the electrosurgical generator 101, if more than one electrosurgical instrument is subsequently plugged into the electrosurgical generator 101 during the medical procedure.

The controller 201 may identify the serial number of the first electrosurgical instrument that is plugged into or operably coupled to the electrosurgical generator 101 or may receive the serial number. For example, once a first electrosurgical instrument is plugged into or operably coupled to the electrosurgical generator 101, the ports unit 203 transmits information associated with the first electrosurgical instrument to the controller 201, and the controller 201 identifies the serial number of the first electrosurgical instrument based on the information received from the ports unit 203. In another embodiment, the controller 201 may receive the serial number of the first electrosurgical instrument. For example, the ports unit 203 identifies the serial number of the first electrosurgical instrument and transmits the serial number to the controller 201.

The controller 201 may be configured to search for or identify the serial number of the electrosurgical generator 101. In some embodiments, the serial number of the electrosurgical generator 101 may be stored in a memory or a storage device of the electrosurgical generator 101 and the controller 201 may be configured to retrieve the serial number from the memory or the storage device. The controller 201 is further configured to determine the date and time at which the first electrosurgical instrument is plugged into the electrosurgical generator 101. For example, the controller 201 may determine the date and time at which the first electrosurgical instrument is plugged into the electrosurgical generator 101 based on the system time of the electrosurgical generator 101 when the controller 201 receives a signal or data message that the electrosurgical instrument is plugged into or operably coupled to the electrosurgical generator 101.

The controller 201 is further configured to store the unique identifier for the medical procedure as an entry in the log file 209 and the alert file 208, such that any entry in the log file 209 and the alert file 208 that follows entry of the unique identifier is identified as data that corresponds to the usage of the electrosurgical instruments and the electrosurgical generator during the medical procedure. In other words, the entries in the log file 208 that follow the entry of the unique identifier describe how the electrosurgical instruments and the electrosurgical generator were used during a medical procedure. In embodiments where a different log file and a different alert file is created for each of the unique electrosurgical instruments, the controller 201 stores the unique identifier for the medical procedure as an entry in each of the log file and alert file.

The controller 201 is configured to transmit the generated unique identifier to the output unit 210. In some embodiments, the output unit 210 may be a display, such as display 101*a*, and the display is configured to display the generated unique identifier. In some embodiments, the output unit 210 may include a NFC tag device and the controller 201 is configured to store the generated unique identifier in the NFC tag device. In some embodiments, the output unit 210 may also include a RFID tag device and the controller 201 is configured to store the generated unique identifier in the RFID tag device. In some embodiments, the output unit 210 may include other types of wireless communication devices and the controller 201 may be further configured to encapsulate the unique identifier in packets using wireless communication protocols compatible with the wireless communication devices.

In embodiments where the output unit 210 is a display, the controller 201 may be configured to encode the generated unique identifier. In some embodiments, the unique identifier may be encoded by converting, incorporating, or translating the unique identifier into a machine-readable representation of the unique identifier, such as linear barcodes, two dimensional barcodes, etc. The controller 201 is further configured to transmit the encoded unique identifier to the display of the electrosurgical generator 101, such as display 101*a*, in order to present the encoded unique identifier to a clinician or a user. An example of an encoded unique identifier being presented for associating the instrument usage data during a medical procedure with the outcome data of the medical procedure is depicted in FIG. 3A.

Figure 3A:
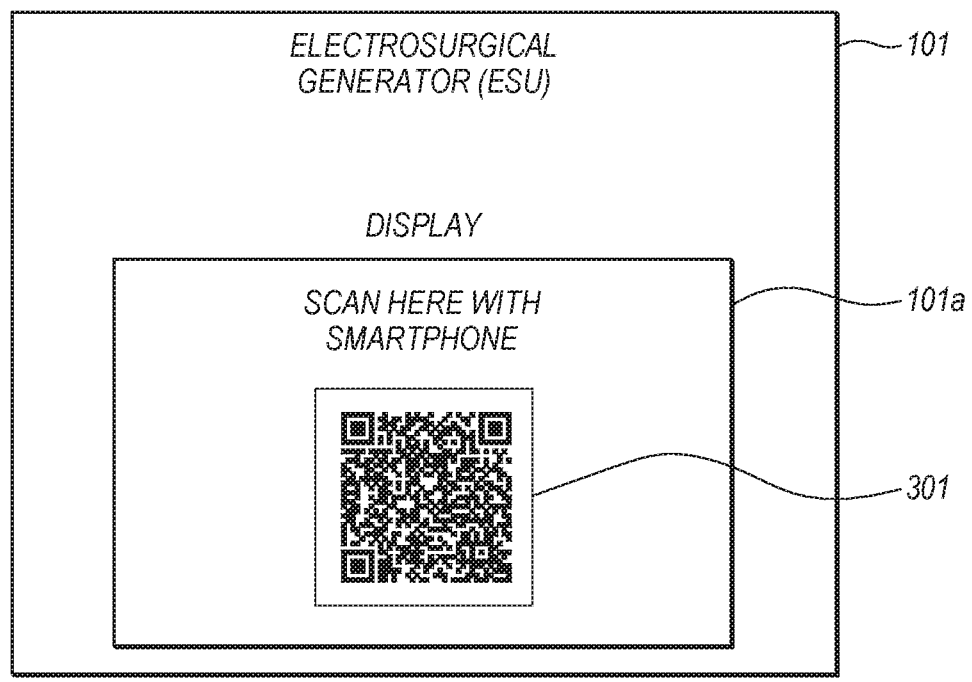
FIG. 3A is a screenshot of a unique identifier displayed on a display of an electrosurgical generator that may be used in the integrated surgical system of FIG. 1, in accordance with an embodiment of the present disclosure.

FIG. 3A depicts the electrosurgical generator 101 displaying an encoded unique identifier 301 on the display of the electrosurgical generator 101. The encoded unique identifier 301 is a QR Code, a type of two dimensional barcode. In some embodiments, the electrosurgical generator 101 may also display an instruction, while displaying the encoded unique identifier, to receive and associate the unique identifier with the outcome data associated with the medical procedure. For example, the controller 201 transmits a message that provides a brief description of the actions a clinician should take in order to receive the unique identifier. In FIG. 3A, the clinician is alerted to use a suitable device to scan the unique identifier 301 in order to receive the encoded unique identifier 301 to be eventually associated with the instrument usage data during the medical procedure with the outcome data of the medical procedure.

Similarly, in embodiments where the output unit 210 includes a RFID tag, NFC tag, and/or other wireless communication devices, the controller 201 may be further configured to transmit a message or an alert that alerts the clinician that a unique identifier for the medical procedure has been generated by the electrosurgical generator 101 and stored in a device, such as the RFID tag, the NFC tag, or the other wireless communication devices, from which the clinician may receive the unique identifier. The message or alert may also include one or more actions the clinician should take to receive the unique identifier.

The handheld computing device 102 may be used to receive the unique identifier. In an embodiment, the handheld computing device 102 includes an image capturing apparatus (not shown), such as a camera, and is configured to capture various types of images including images of machine-readable representations of data, such as linear barcodes, two-dimensional barcodes (e.g., a QR Code). In some embodiments, the handheld computing device 102 includes instructions stored in its memory (not shown) to decode images of the various types of machine-readable representations of data, such as linear barcodes, two-dimensional barcodes and retrieve or identify the information stored in the image. The handheld computing device 102 may communicatively couple to electrosurgical generator 101 by capturing an image of the information displayed on display 101*a*. In another embodiment, the handheld computing device 102 may additionally or alternatively include a RFID reader and receive information stored in the RFID tag of the electrosurgical generator 101. In still another embodiment, the handheld computing device 102 may additionally or alternatively include a NFC reader and communicate with the electrosurgical generator 101 by receiving information stored in the NFC tag of the electrosurgical generator 101. The handheld computing device 102 may alternatively be configured with other wireless communication devices to receive or transmit data using one or more wireless communication protocols that are compatible for receiving and/or transmitting data with other computing devices configured with wireless communication devices.

Figure 3B:
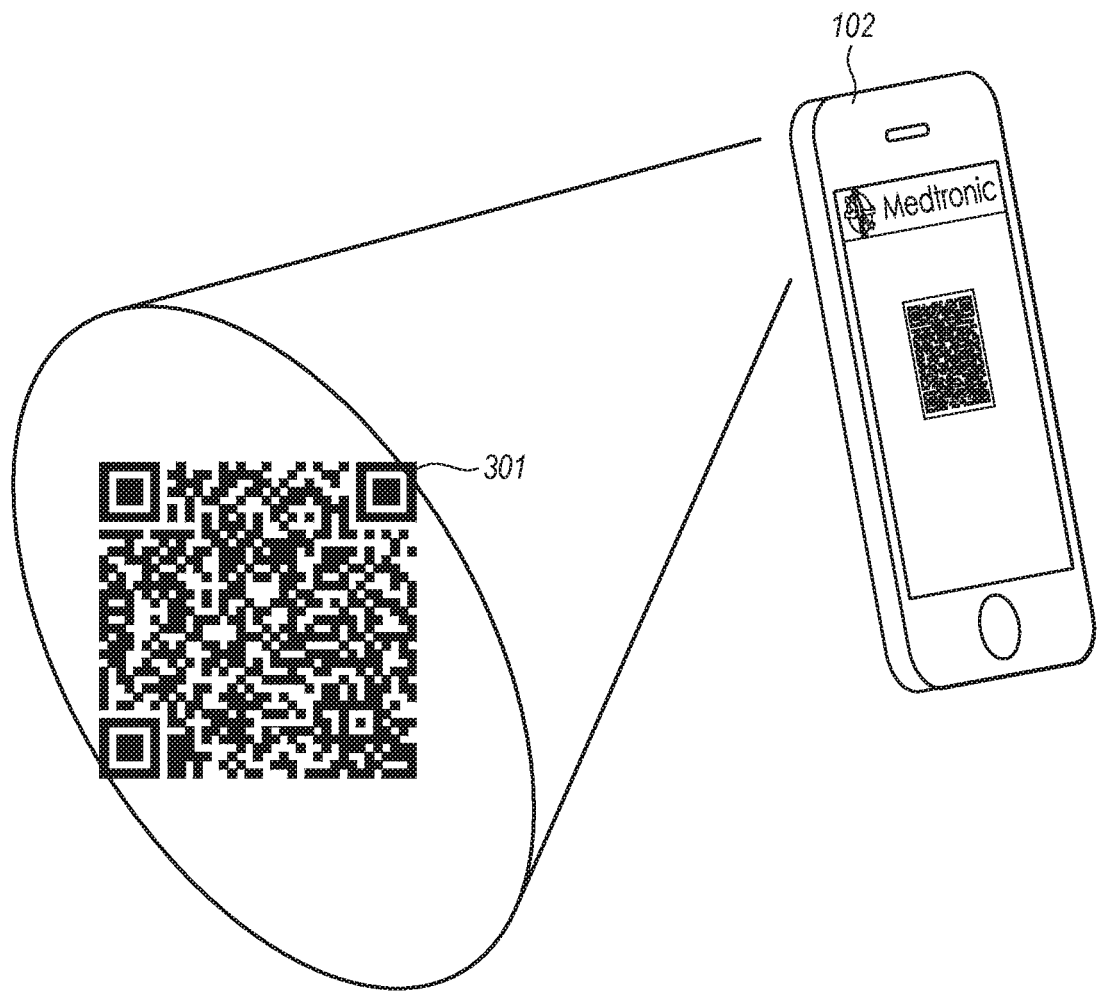
FIG. 3B is a schematic illustration of a handheld computing device including a display of a unique identifier being scanned, in accordance with an embodiment of the present disclosure.

An example of how a clinician may receive the unique identifier in order to associate the unique identifier with the outcome data of the medical procedure is depicted in FIG. 3B. For example, using the image capturing apparatus of the handheld computing device 102, an image of the encoded unique identifier 301 is captured and received by the handheld computing device 102 and the image of the encoded unique identifier 301 is received by the handheld computing device 102. In some embodiments, the encoded unique identifier 301 may comprise data additional to the unique identifier, such as, information about one or more alerts generated by electrosurgical instrument 101, settings of the electrosurgical instrument when the encoded unique identifier 301 is generated, and the like. In some embodiments, the handheld computing device 102 may include instructions stored thereon to decode the encoded unique identifier 301 in order to retrieve the information included in the encoded unique identifier 301.

While FIG. 3B depicts the handheld computing device 102 receiving the unique identifier 301 using an image capturing apparatus, the handheld computing device 102 is configured to also receive the unique identifier 301 wirelessly. As described above, the handheld computing device 102 may be configured with a RFID reader, a NFC reader or other wireless communication device. In embodiments where the unique identifier is stored in the RFID tag or NFC tag, the handheld computing device 102 may receive the unique identifier using the RFID reader or the NFC reader, respectively. Similarly, in embodiments where the unique identifier is stored in other types of wireless communication devices, the handheld computing device 102 receives the unique identifier using a wireless communication protocol compatible with the wireless communication device storing the unique identifier and the wireless communication device on the handheld computing device 102.

The handheld computing device 102 is further configured to be used to associate the encoded unique identifier 301 with the outcome data of the medical procedure on the handheld computing device 102. In particular, the outcome data corresponding to the medical procedure is entered into the handheld computing device 102.

Figure 4A:
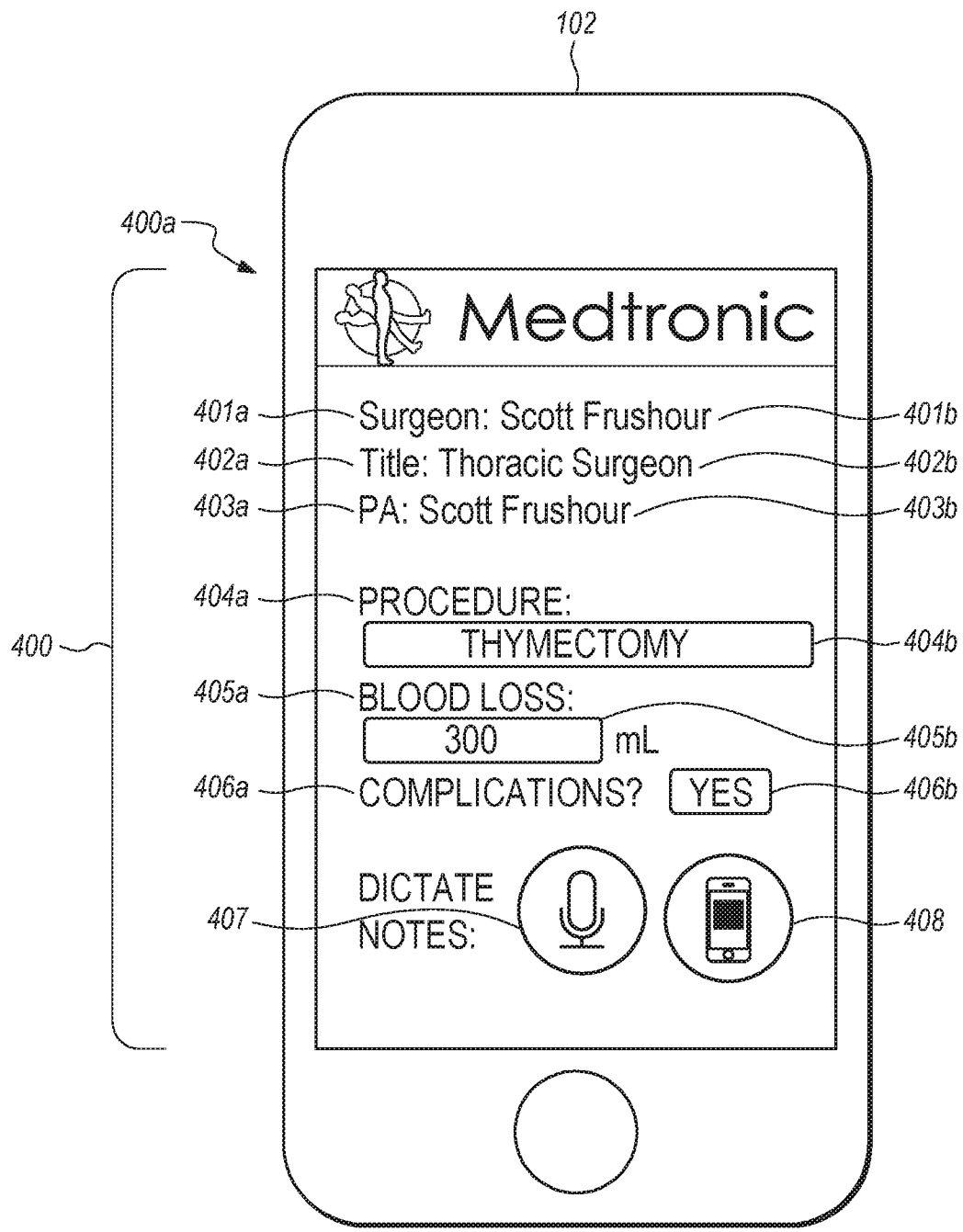
FIG. 4A is a graphical user interface on a screen of a handheld device for receiving outcome data and associating a unique identifier with the outcome data, in accordance with an embodiment of the present disclosure.

Turning now to FIG. 4A, additional details of associating the outcome data of the medical procedure with the data corresponding to instrument usage during the medical procedure are described with respect to FIG. 4A. Here, the handheld computing device 102 is configured to provide a user interface to associate the unique identifier with received outcome data corresponding to the medical procedure. The association of the outcome data with unique identifier generated by the electrosurgical generator 101 is later used to associate the outcome data with the instrument usage data on the electrosurgical generator 101. The handheld computing device 102 includes one or more processors (not shown) that are operably connected to one or more of a memory (not shown). The memory may be any type of hardware device used to store data including instructions, which, when executed by the one or more processors of the handheld computing device 102, cause the handheld computing device 102 to perform the one or more operations or techniques described herein. The memory may be volatile memory, non-volatile memory, magnetic storage media, optical storage media or electrical media. The one or more processors may be any type of suitable processors that are adapted to perform the techniques or operations or execute instructions described herein, such as general hardware processors, ASICs, FPGAs, DSPs, microprocessors, etc.

The handheld computing device 102 includes an operating system (not shown). The handheld computing device 102 also includes one or more applications and the one or more applications, including application 400, are compatible with the operating system and may utilize one or more functionalities provided by the operating system to perform one or more tasks that the applications are configured to perform. The application 400 includes a graphical user interface 400a for receiving inputs to the application 400. The graphical user interface 400a includes a plurality of graphical items. As described above, the term "graphical items" includes, but is not limited to, images, graphical labels, data entry mechanisms, such as text boxes, radio buttons, drop down lists, drop down menus, etc., or combinations thereof. The graphical user interface 400a is configured to present data and receive input from the clinician using a plurality of the graphical items. As shown in FIG. 4A, the graphical user interface 400a may present the name of a surgeon using label 401a and text box 401b, the title of the surgeon using label 402a and text box 402b, the name of a staff member assisting the surgeon using label 403a and text box 403b.

The handheld computing device 102 may be communicatively coupled, via a network 410 (shown in FIG. 4B), to a scheduling system 413 (shown in FIG. 4B) of the medical facility where the medical procedure is being performed and certain information, such as names of the surgeons or staff members or both, title of the surgeons or staff members, etc., may be auto-populated. Alternatively, the graphical user interface 400a may prompt the user to enter such information through a series of prompts or by providing empty text boxes or unselected drop down lists.

The graphical user interface 400a also presents graphical items to receive outcome data of the medical procedure from a clinician. For example, as shown in FIG. 4A, the graphical user interface 400a presents graphical items 404a to indicate to a clinician to enter the medical procedures performed and 404b to receive data regarding the medical procedures performed. Similarly, graphical item 405a is presented to indicate to a clinician to enter blood loss data and 405b is presented to receive blood loss data, and graphical items 406a and 406b are presented to indicate to a clinician to enter any complications experienced during the medical procedures and receive data regarding the complications, respectively. The graphical user interface 400a may also present other graphical items to receive data regarding various other outcome data or anonymized patient data including, but not limited to, height, weight, and other anonymized health attributes of the patient and an indication of how successful the outcome is to be considered.

The graphical user interface 400a may present graphical items to indicate to the surgeon that he/she may record his/her surgical notes via dictation and the application 400 may be configured to access the microphone of the handheld computing device 102 when the surgeon interacts with the graphical item. For example, graphical item 407, as shown in FIG. 4A, includes an image of a microphone to indicate to the surgeon that by clicking on the graphical item 407, the surgeon may begin recording surgical notes orally. The graphical user interface 400a may use other graphical items to present other options to receive notes of the surgeon regarding the medical procedure.

The graphical user interface 400a may also present graphical items, such as graphical item 408, to indicate to the clinician that by interacting with the graphical item, the unique identifier generated by the electrosurgical generator 101 may be received. The application 400 may be configured to access image capturing apparatus, RFID reader, NFC reader, or other wireless communication device of the handheld computing device 102 when the corresponding graphical items that indicate the capture or reception of the unique identifier are interacted with, selected or clicked. For example, when graphical item 408 is selected, the application 400 accesses the image capturing apparatus of the handheld computing device 102 to capture the image of the unique identifier displayed on the electrosurgical generator 101.

The application 400 may be further configured to store the received outcome data and the received unique identifier into the memory of the handheld computing device 102. In some embodiments, the application 400 may present a confirmation screen to the clinician prior to the storing the received outcome data or the received unique identifier.

Figure 4B:
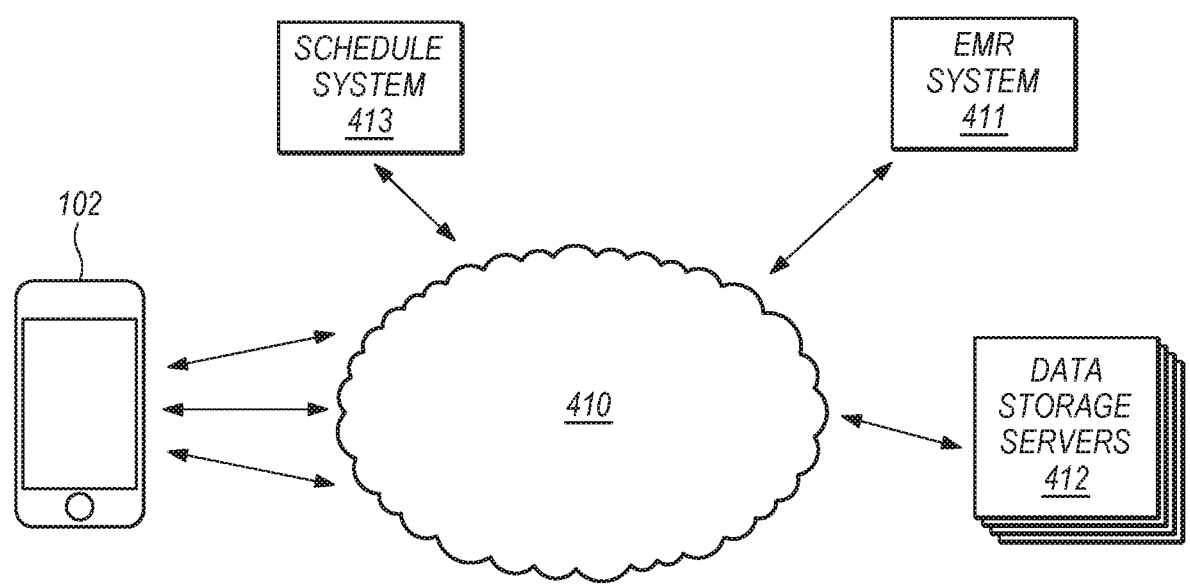
FIG. 4B is a schematic of a handheld computing device communicatively coupled to one or more data stores and one or more electronic medical record systems.

Referring now to FIG. 4B, the handheld computing device 102 may be communicatively coupled, via a network 410, to an electronic medical record (EMR) system 411 that comprises the EMR of the patient P and/or to one or more data storage servers 412 at a data storage facility of the medical device manufacturer. Examples of the network 410 include, but are not limited to, a wireless network, a telecommunications network, or other types of computer networks. Examples of the data storage facility include, but are not limited to, a data mart or data center. The handheld computing device 102, through the application 400, may be further configured to transmit the stored outcome data to the EMR system 411 in order to complete the EMR of the patient P. The handheld computing device 102 may transmit the stored outcome data and the associated unique identifier to one or more data storage servers 412 of the medical device manufacturer, thus providing the medical device manufacturer the outcome data for the medical procedure performed using the electrosurgical generator manufactured by the medical device manufacturer.

As described above, the unique identifier generated by the electrosurgical generator 101 and received by the handheld computing device 102 is also logged or included in the alert file 208 and the log file 209. A system of the medical device manufacturer may access the alert file 208 and the log file 209 from the electrosurgical generator 101 and retrieve the corresponding instrument usage data, based on the unique identifier received from the handheld computing device 102. For example, a system of the medical device manufacturer may search for the unique identifier received from the handheld computing device 102 in the alert file 208 and the log file 209 to identify data corresponding to the usage of the electrosurgical instruments used in system 100 and the electrosurgical generator 101 during the medical procedure. Then, the system, using the unique identifier generated by the electrosurgical generator 101 and received from the handheld computing device 102, associates the outcome data of the medical procedure, received from the handheld computing device 102, with the data corresponding to the instrument usage during the medical procedure, identified in the alert file 208 and log file 209. Thus, the medical device manufacturer is able to associate, for a given medical procedure, a specific unique outcome with certain instrument usage.

Figure 5:
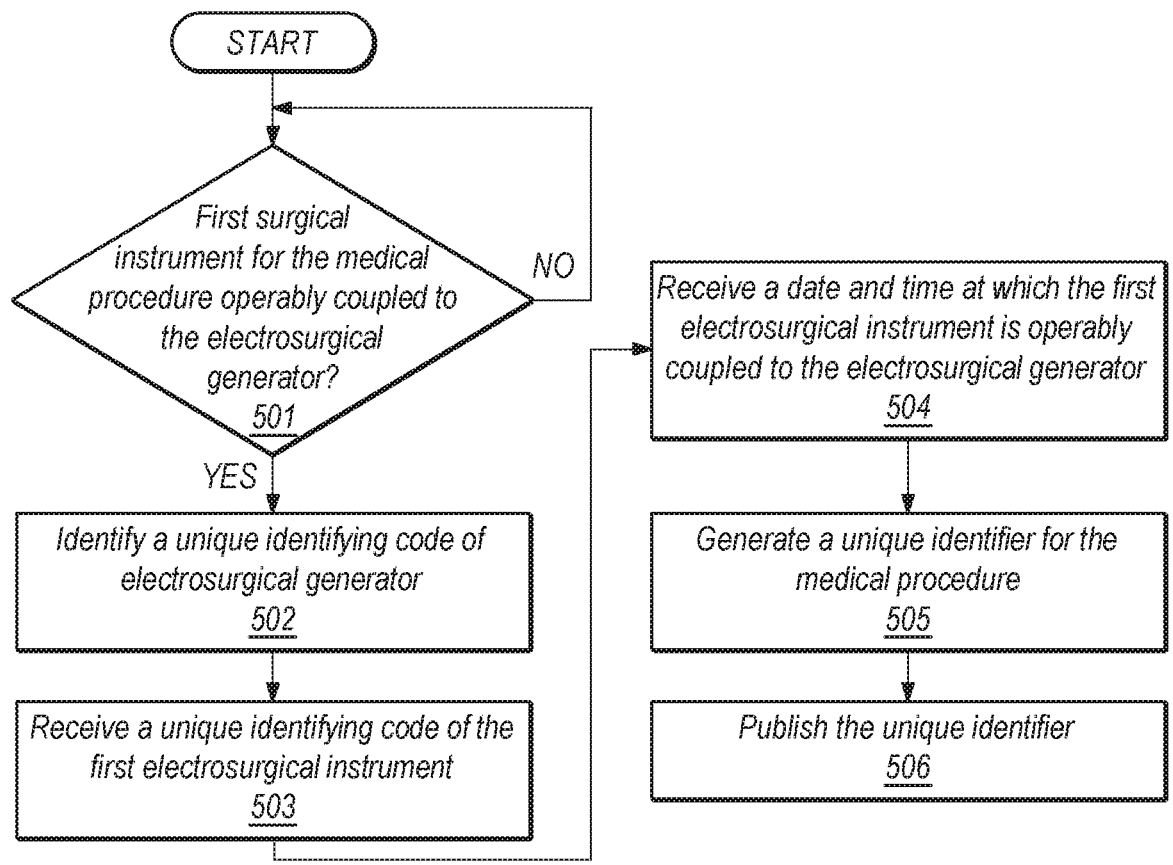
FIG. 5 is a flow diagram of a method of generating a unique identifier, in accordance with an embodiment of the present disclosure.

Turning now to FIG. 5, creation of the unique identifier is provided by method 500. In an embodiment, the operations described for FIG. 5 may be performed by the controller 201 of FIG. 2 or FIG. 3A, but other embodiments may implement the same functions in other contexts using other computing devices. In step 501, whether a first surgical instrument for the medical procedure is operably coupled to the electrosurgical generator or not is determined. For example, the controller 201 may receive a signal or a message indicating that an electrosurgical instrument is plugged into the electrosurgical generator 101. In some embodiments, the controller 201 may update a flag variable that indicates whether an electrosurgical instrument that is plugged into the electrosurgical generator 101 is a first electrosurgical instrument of a series of electrosurgical instruments to be plugged in for the medical procedure or a subsequent electrosurgical instrument. For example, the value of the flag variable may be initially set to zero to indicate that no electrosurgical instruments have been plugged into the electrosurgical generator and after an electrosurgical instrument is plugged into the electrosurgical generator, the controller 201 may check the value of the flag variable and if the value is zero, then the controller 201 determines that the electrosurgical instrument is the first electrosurgical instrument and sets the value of the flag variable to one.

The controller 201 then initiates the process of creating a unique identifier for the medical procedure. In this regard, in step 502, a unique identifying code of the electrosurgical generator is identified. As described above, the unique identifying code may be a serial number of the electrosurgical generator. The unique identifying code of the electrosurgical generator may be stored in memory accessible by the controller 201 and the controller 201 accesses the memory to retrieve the unique identifying code. Continuing with the creation of the unique identifier for the medical procedure, in step 503, a unique identifying code of the first electrosurgical instrument is received. In some embodiments, the controller 201 may determine or identify the unique identifying code of the first electrosurgical instrument based on certain characteristics of the electrosurgical instrument and by searching through a lookup table comprising the characteristics and a corresponding serial number of the electrosurgical instrument.

In step 504, the date and time at which the first electrosurgical instrument is operably coupled to the electrosurgical generator is received. In some embodiments, the date and time is determined by the controller 201. For example, the ports unit 203 may be operably coupled to the system clock of the electrosurgical generator and determines the date and time at which an electrosurgical instrument is plugged into the electrosurgical generator and transmits the date and time to the controller 201. The controller 201 determines whether the electrosurgical instrument plugged into the electrosurgical generator is a first electrosurgical instrument and if the electrosurgical instrument is the first electrosurgical instrument, then the controller uses the date and time in the creation of the unique identifier for the medical procedure.

In step 505, a unique identifier is generated using the unique identifying code of the electrosurgical generator, the unique identifying code of the first electrosurgical instrument, and the date and time at which the first electrosurgical instrument is operably coupled to the electrosurgical generator. In some embodiments, the unique identifier may be encoded into machine-readable representations, such as single or multi-dimensional barcodes. In step 506, the unique identifier is published. As described above, the term "publish" refers to making data available for consumption or retrieval by other computing devices. In some embodiments, the unique identifier is published by displaying the unique identifier on a display screen. In some embodiments, the unique identifier is published by storing the unique identifier in a wireless communication device on the electrosurgical generator including, but not limited to, RFID tags, NFC tags, etc.

Figure 6:
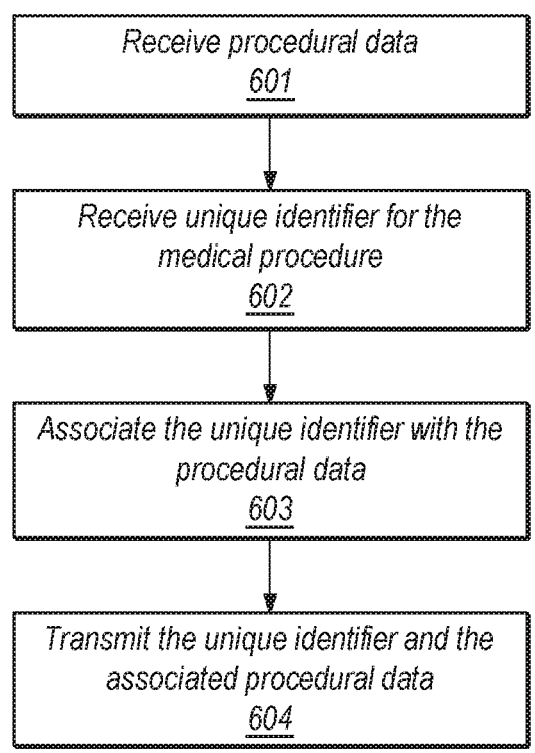
FIG. 6 is a flow diagram of a method of associating a unique identifier with outcome data, in accordance with an embodiment of the present disclosure.

Turning now to FIG. 6, associating the unique identifier with the outcome data of the medical procedure is provided by method 600. In an embodiment, the operations described for FIG. 6 may be performed by the handheld computing device 102 described herein, but other embodiments may implement the same functions in other contexts using other computing devices. In step 601, outcome data of the medical procedure is received. The outcome data may include information regarding the names of the surgeons and staff members, the vitals of the patient when the medical procedure began, the vitals of the patient when the medical procedure ended, and physiological markers of the patient, such as height, weight, etc. The outcome data may also include information corresponding to the type of medical procedure or procedures that were performed on the patient. The outcome data may also include data related to any extraordinary or emergency steps that needed to be taken during the procedure, expected recovery time of the patient, and whether the medical procedure was a success, a failure, or neither a success nor a failure. As described above, the outcome data may be input from a clinician or auto-populated.

In step 602, the unique identifier for the medical procedure is received. In some embodiments, the unique identifier is received by the capturing an image of the unique identifier by the handheld computing device 102, and the handheld computing device 102 may be configured to perform optical character recognition (OCR) to identify the characters that makeup the unique identifier. In some embodiments, the handheld computing device 102 may be configured to decode the various types of barcodes, including linear and multi-dimensional barcodes to identify the characters that makeup the unique identifier. The handheld computing device 102 may store the decoded unique identifier or the characters identified from the unique identifier using the OCR process. In some embodiments, the handheld computing device 102 receives the unique identifier using wireless communication devices such as RFID readers, NFC readers, etc., by bringing the handheld computing device 102 within a threshold distance of the computing device storing the unique identifier, such as the electrosurgical generator. For example, where the unique identifier is stored in a NFC tag of the electrosurgical generator and the handheld computing device 102 is configured with a NFC reader, the handheld computing device 102 may be placed within a few centimeters of the location of the NFC tag of the electrosurgical generator or may tap the NFC tag of the electrosurgical generator or may tap a designated location on the electrosurgical generator to receive the unique identifier.

In step 603, the unique identifier and the outcome data are associated with each other. In some embodiments, a mapping relationship may be created between the outcome data and the unique identifier such that all outcome data associated with the unique identifier may be identified or retrieved by searching for the unique identifier only. Similarly, the unique identifier associated with the outcome data may be identified by querying the outcome data for the unique identifier. In embodiments, where an image of the encoded unique identifier is associated with the outcome data, an image search for the image of the encoded unique identifier may be performed to identify the associated outcome data. In some embodiments, a clinician may be prompted to confirm whether he or she wishes to associate the received unique identifier with the outcome data prior to associating the unique identifier with the outcome data.

In step 604, the unique identifier and the associated outcome data are transmitted to an external system. The external system may be under the control of a medical device manufacturer or accessible by the medical device manufacturer. In some embodiments, the transmission of the unique identifier and the associated outcome data may occur after an input indicating the initiation of the transmission is received. For example, a clinician may be presented a graphical item (not shown) on the graphical user interface 400a of the application 400 on the handheld computing device 102, which indicates to the clinician that the selection of or clicking on the graphical item may initiate the transmission process of the unique identifier and the associated outcome data to the system. The transmission process may be performed by an application, such as application 400, of the handheld computing device 102 using a wireless communication device of the handheld computing device 102 and a compatible wireless communication protocol.

Using the techniques described herein, a medical device manufacturer may identify correlations between how medical instruments are used during a medical procedure and the outcome of the medical procedure. Similarly, the medical device manufacturer may also identify correlations between the type of medical instruments used and the outcome of the medical procedure. Furthermore, a plurality of correlations, identified from different instrument usage data and their associated outcome data from different time periods, may be analyzed to identify specific instrument usage patterns that helped deliver certain desirable outcomes to the health of the patient. Using such data, the medical device manufacturer may identify the precise areas of improvements in its existing portfolio of medical instruments and devices. Using such data, the medical device manufacturer may also identify new product categories to fill in any identified gaps in performance of medical procedures.

Additionally, the analysis of the specific instrument usage patterns may be shared with clinicians or medical facility administrators in order to implement the instrument usage techniques while the clinicians perform the medical procedure. Using the correlation data or the specific instrument usage data or both, surgical skills of a surgeon may be evaluated and quantified measurements of the surgical skills may be presented to the surgeon in order to improve surgical skills or the process with which the surgeon approaches a particular medical procedure. Furthermore, the techniques described herein, utilize anonymized patient data. Thus, compliance with various patient privacy laws and regulations, such as Health Insurance Portability and Accountability Act (HIPAA), is easily satisfied.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for use during a medical procedure, the system comprising:
    a surgical instrument associated with an instrument identifier; and
    an electrosurgical generator operably coupled to the surgical instrument, wherein the electrosurgical generator includes a generator identifier and is configured to:
        receive and store an operating mode of the surgical instrument;
        receive the instrument identifier from the surgical instrument;
        generate a unique identifier, different from the generator identifier and the instrument identifier and which is generated after the surgical instrument is operably coupled to the electrosurgical generator for the first time, based on:
            a time and date at which the surgical instrument is operably coupled with the electrosurgical generator for the first time;
            the generator identifier of the electrosurgical generator; and
            the instrument identifier; and
        associate the unique identifier with the operating mode of the surgical instrument.

2. The system of claim 1, wherein the electrosurgical generator includes a wireless communication device, wherein the generator is further configured to store the unique identifier in a storage device accessible for wireless communication by the wireless communication device.

3. The system of claim 2, wherein the wireless communication device is at least one of a radio frequency identification tag or a near field communication tag.

4. The system of claim 1, wherein the generator identifier includes a serial number of the electrosurgical generator.

5. The system of claim 1, wherein the instrument identifier includes a serial number of the surgical instrument.

6. The system of claim 1, wherein the electrosurgical generator is further configured to record the time and date at which the surgical instrument is operably coupled with the electrosurgical generator for the first time.

7. The system of claim 1, wherein:
    the electrosurgical generator is further configured to store real-time data related to the surgical instrument during the medical procedure, and
    associate the unique identifier with the stored real-time data related to the surgical instrument.

8. The system of claim 1, wherein:
    the electrosurgical generator further includes a display, and is further configured to display the unique identifier on the display.

9. The system of claim 8, further comprising:
    a handheld computing device including an image capture device, a processor, and a memory, the memory having instructions stored thereon which, when executed, cause the handheld computing device to:
        capture an image of the unique identifier displayed on the display of the electrosurgical generator; and
        associate the captured image of the unique identifier to outcome data of the medical procedure.

10. The system of claim 9, wherein the instructions stored on the memory of the handheld computing device further cause the handheld computing device to display a graphical user interface including input buttons for inputting the outcome data of the medical procedure.

11. The system of claim 1, wherein the unique identifier is further based on an alert generated by the surgical instrument.

12. The system of claim 1, wherein the unique identifier is further based on a setting of the surgical instrument.

13. A method of operating a surgical system during a medical procedure, the method comprising:
    receiving an operating mode of a surgical instrument;
    storing the operating mode of the surgical instrument;
    receiving an instrument identifier from the surgical instrument;
    generating a unique identifier, different from the instrument identifier and which is generated after the surgical instrument is operably coupled to an electrosurgical generator for the first time, based on:
        a time and date at which the surgical instrument is operably coupled with the electrosurgical generator for the first time;
        a generator identifier of the electrosurgical generator; and
        the instrument identifier; and
    associating the unique identifier with the stored operating mode of the surgical instrument.

14. The method of claim 13, further comprising:
    storing the unique identifier in a storage device operably coupled to a wireless communication device.

15. The method of claim 14, wherein the wireless communication device is at least one of a radio frequency identification tag or a near field communication tag.

16. The method of claim 13, wherein the generator identifier includes a serial number of the electrosurgical generator.

17. The method of claim 13, wherein the instrument identifier includes a serial number of the surgical instrument.

18. The method of claim 13, further comprising:
recording the time and date at which the surgical instrument is operably coupled with the electrosurgical generator for the first time.

19. The method of claim 13, further comprising:
storing real-time data related to the surgical instrument during the medical procedure; and
associating the unique identifier with the stored real-time data related to the surgical instrument.

20. The method of claim 19, further comprising:
displaying the unique identifier on a display of the electrosurgical generator.

21. The method of claim 20, further comprising:
capturing, using an image capturing apparatus of a handheld computing device, an image of the unique identifier displayed on the display of the electrosurgical generator; and
associating the captured image of the unique identifier to outcome data of the medical procedure.

22. The method of claim 21, further comprising:
on the handheld computing device, displaying a graphical user interface including input buttons for inputting outcome data of the medical procedure.

* * * * *